United States Patent
Zhang et al.

(10) Patent No.: US 8,574,838 B2
(45) Date of Patent: Nov. 5, 2013

(54) METHODS AND KITS FOR MIRNA ISOLATION AND QUANTITATION

(75) Inventors: Chunxiang Zhang, Short Hills, NJ (US); Yunhui Cheng, Kearny, NJ (US); Xiaojun Liu, Harrison, NJ (US); Jian Yang, Short Hills, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 1 day.

(21) Appl. No.: 13/182,480

(22) Filed: Jul. 14, 2011

(65) Prior Publication Data

US 2012/0034612 A1    Feb. 9, 2012

Related U.S. Application Data

(60) Provisional application No. 61/364,351, filed on Jul. 14, 2010.

(51) Int. Cl.
*C12Q 1/68* (2006.01)

(52) U.S. Cl.
USPC ....... 435/6.1; 536/23.1; 536/24.33; 435/91.1; 435/91.2

(58) Field of Classification Search
None
See application file for complete search history.

(56) References Cited

U.S. PATENT DOCUMENTS 6,806,046 B2 * 10/2004 Johnston-Dow et al. ......... 435/5

OTHER PUBLICATIONS

Stratagene Micro RNA Isolation Kit, 2002.*
Ai J, Zhang R, Li Y, Pu J, Lu Y, Circulating microRNA-1 as a potential novel biomarker for acute myocardial infarction, Biochem Biophys Res Commun, 391: 73-77, Epub. Nov. 5, 2009.*
miRNA 1st-Strand cDNA Synthesis Kit, Jan. 2009.*
High Specificity miRNA QPCR Core Reagent Kit, Jan. 2010.*
The Power You Need to Fuel Your microRNA Research, Mar. 2008.*
Lu Y, Zhang Y, Shan H, Pan Z, Li X, Li B. et al., MicroRNA-1 downregulation by propranolol in a rat model of myocardial infarction: a new mechanism for ischaemic cardioprotection, Cardiovasc Res., 2009;84:434-41, Epub Jul. 6, 2009.*
Lu et al, Supplemental Materia, Jul. 6, 2009.*
Chen et al. "Characterization of MicroRNAs in Serum: A Novel Class of Biomarkers for Diagnosis of Cancer and Other Diseases" Cell Research 2008 vol. 18: 997-1006.
Cheng et al. "MicroRNA-145, A Novel Smooth Muscle Cell Phenotypic Marker and Modulator, Controls Vascular Neointimal Lesion Formation" Circulation Research 2009 vol. 105:158-166.
Cortez, M.A. and Calin, G.A. "MicroRNA Identification in Plasma and Serum: A New Tool to Diagnose and Monitor Diseases" Expert Opinion on Biological Therapy 2009 vol. 9:703-711.
Dong et al. "MicroRNA Expression Signature and the Role of MicroRNA-21 in the Early Phase of Acute Myocardial Infarction" The Journal of Biological Chemistry 2009 vol. 284(43) :29514-29525.
Ji et al. "MicroRNA Expression Signature and Anitsense-Mediated Depletion Reveal an Essential Role of MicroRNA in Vascular Neointimal Lesion Formation" Circulation Research 2007 vol. 100:1579-1588.

* cited by examiner

*Primary Examiner* — Christopher M Babic
*Assistant Examiner* — Aaron Priest
(74) *Attorney, Agent, or Firm* — Licata & Tyrrell, P.C.

(57) ABSTRACT

The present invention is a kit and method for isolating and quantitating miRNA and to the use of such methods in the diagnosis and prognosis of disease.

5 Claims, 1 Drawing Sheet

SEQUENCE LISTING

<160> NUMBER OF SEQ ID NOS: 1

<210> SEQ ID NO 1
<211> LENGTH: 55
<212> TYPE: DNA
<213> ORGANISM: Artificial sequence
<220> FEATURE:
<223> OTHER INFORMATION: Synthetic oligonucleotide

<400> SEQUENCE: 1
gtcgtatcca gtgcgtgtcg tggagtcggc aattgcactg gatacgacta catac        55

METHODS AND KITS FOR MIRNA ISOLATION AND QUANTITATION

This application claims priority to U.S. Provisional Application No. 61/364,351, filed Jul. 14, 2010, which is incorporated herein by reference.

This invention was made with government support under grant numbers HL080133 and HL095707 awarded by the National Institutes of Health. The government has certain rights in the invention.

BACKGROUND OF THE INVENTION

The presence of microRNAs (miRNAs) in both human and animal circulating blood has been reported (Chen, et al. (2008) Cell Res. 18:997-1006). Serum or plasma miRNAs may serve as novel clinical biomarkers for diverse diseases, because the levels of these cell-free serum miRNAs are significantly changed in human under disease conditions (Cortez & Calin (2009) Expert Opin. Biol. Ther. 9:703-711).

MicroRNAs are endogenous non-coding single-stranded RNAs of approximately 22 nucleotides in length and constitute a novel class of gene regulators (Chua, et al. (2009) Curr. Opin. Mol. Ther. 11:189-199). Analogous to the first RNA revolution in the 1980s (Zaug & Cech (1986) Science 231: 470-475), the more recent discoveries of RNAi (RNA interference) and miRNA may represent the second RNA revolution. Although the first miRNA, lin-4, was discovered in 1993 (Lee, et al. (1993) Cell 75:843-854; Wightman, et al. (1993) Cell 75:855-862), their presence in vertebrates was only confirmed in 2001 (Lagos-Quintana, et al. (2001) Science 294: 853-858). Currently, approximately 800 miRNAs have been cloned and sequenced in humans (Bentwich, et al. (2005) Nat. Genet. 37:766-770), and the estimated number of miRNA genes is as high as 1000 in the human genome (Lewis, et al. (2005) Cell 120:15-20).

Mature miRNAs bind to the 3'-UTR (untranslated region) of their mRNA targets and negatively regulate gene expression via degradation or translational inhibition (Chen & Rajewsky (2007) Nat. Rev. Genet. 8:93-103). Functionally, an individual miRNA is important as a transcription factor because it is able to regulate the expression of its multiple target genes. As a group, miRNAs are estimated to regulate over 30% of the genes in a cell. It is thus not surprising that miRNAs are involved in the regulation of almost all major cellular functions, including apoptosis and necrosis. Accordingly, miRNAs may be involved in many diseases, including cardiovascular disease (Zhang (2008) Clin. Sci. 114:699-706; Zhang (2008) Physiol. Genomics 33:139-147).

Tissue- and cell-specific expression is one important characteristic of miRNA expression (Lagos-Quintana, et al. (2002) Curr. Biol. 12:735-739). Indeed, one miRNA may be highly expressed in one tissue or one cell, but has no or low expression in other tissues or cells. For example, miR-1 is reported to be a muscle or heart-specific miRNA, whereas miR-145 is a vascular smooth muscle cell-specific miRNA (Cheng, et al. (2009) Circ. Res. 105:158-166). The tissue-specific miRNA expression and tissue expression signatures of diseases have provided a great diagnostic opportunity for diverse diseases (Dong, et al. (2009) J. Biol. Chem. 284: 29514-29525).

Recent studies have revealed that miRNAs exist in circulating blood (Ji, et al. (2007) Circ. Res. 100:1579-1588). Cell-free miRNAs are relatively stable due to binding with other materials such as exosomes in circulating blood. Moreover, cancer tissue miRNAs are able to be released into circulating blood and serum or plasma cell-free miRNAs can be used as novel biomarkers for diverse cancers. However, a robust quantitative method to measure the absolute amount of a miRNA in blood has not been established due to a lack of stable control RNAs in blood, especially under disease conditions. More importantly, the role of the circulating cell-free miRNAs in patients with cardiovascular diseases is currently unclear. Therefore, there is a need in the art for improved assays for isolating and analyzing miRNAs in biological fluids.

SUMMARY OF THE INVENTION

The present invention provides methods for isolating and quantitating a miRNA from a biological fluid. Isolation of the miRNA involves the steps of (a) mixing a biological fluid containing miRNA with a denaturing solution containing 20-25 mM sodium citrate and glycogen; and (b) extracting the miRNA from the mixture of (a). Quantitation of the miRNA involves the steps of (a) reverse transcribing the miRNA; (b) subjecting the reverse transcribed product of (a) to real time PCR; and (c) comparing the amount of real time PCR product of (b) with a reference amount of mature miRNA. In one embodiment, the amount of miRNA is expressed as mass of miRNA per volume of biological fluid. In another embodiment, the isolation and quantitation method are carried out in tandem. Kits for carrying out the instant methods are also provided, as is a method for diagnosing or prognosing an acute myocardial infarction by quantitating the amount of miR-1 in a blood or plasma sample from a subject and comparing the amount of miR-1 in the subject's sample with the amount of miR-1 in a reference sample.

BRIEF DESCRIPTION OF THE DRAWINGS

FIG. 2 shows that serum miR-1 is increased in patients with AMI.

DETAILED DESCRIPTION OF THE INVENTION

Figure 1:
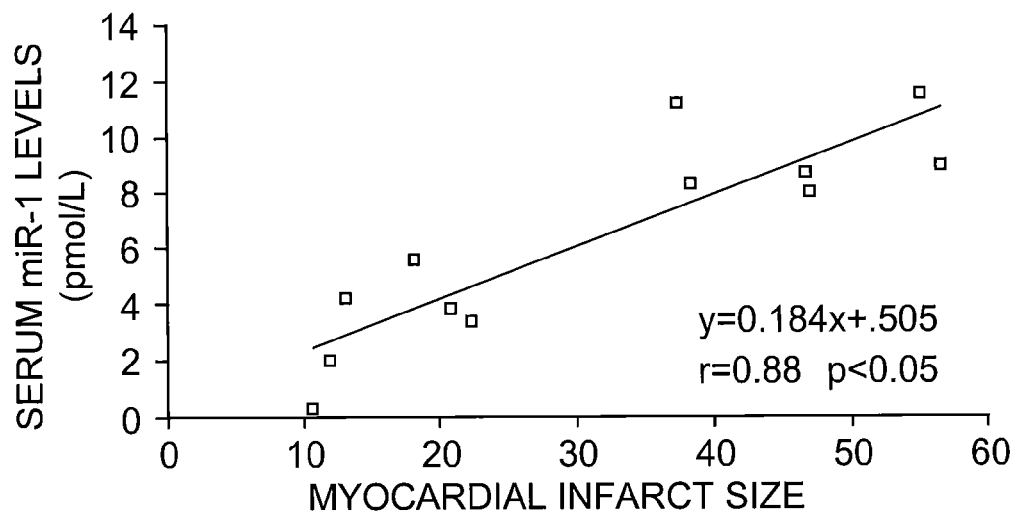
FIG. 1 shows the relationship between serum miR-1 levels and myocardial infarct sizes in rats with AMI. AMI was induced by I/R injury in 12 rats, and the infarct sizes and serum miR-1 levels were determined in rats at 3 hours after reperfusion. A strong positive correlation was demonstrated between the two variables (r=0.88; P<0.05).

The search for new biomarkers of cardiovascular diseases, including acute myocardial infarction (AMI), is of interest. Currently, clinically applied circulating biomarkers are typically peptides or proteins that are analyzed by biochemical or immunoassay techniques. However, it was contemplated that nucleotide-based biomarkers may enhance diagnostic or therapeutic effectiveness. An ideal nucleotide blood biomarker of AMI should be abundant, be preferentially (or exclusively) produced in heart and be present at low concentrations in the blood. Upon AMI, such nucleotides should be released into the circulating blood, where they are relatively stable and can be quickly detected by molecular technologies. It has now been found that serum miR-1 meets the above requirements. In addition, methods for isolating and quantitating the serum level of miRNAs using qRT-PCR (quantitative real-time PCR) have now been established. The potential applications of serum miRNA isolation and detection in acute myocardial infarction (AMI) have also been determined by the translational study from cells to animal and humans.

As is known in the art, miRNA are short ribonucleic acid (RNA) molecules, on average only 22 nucleotides long, and are post-transcriptional regulators that bind to complementary sequences on target messenger RNA transcripts (mRNAs), usually resulting in translational repression and gene silencing. For the purposes of the present invention, "solution miRNA," "cell-free miRNA" or "miRNA in solution" are intended to mean miRNA molecules that are present or free in a biological fluid, e.g., not located intracellularly. Biological fluid samples include blood, plasma, serum, urine, sputum, cerebrospinal fluid, milk, or ductal fluid samples, with particular embodiments embracing blood, plasma and serum.

To facilitate the use of solution miRNAs as biomarkers, methods and kits for isolating miRNA and determining the absolute amount of a cell-free miRNA using qRT-PCR technology were developed. In general, the reagents of the instant isolation method and kit include miRNA denaturing and extraction solutions, which were specially designed for miRNAs in solution. In particular, glycogen and the concentration of sodium citrate in the denaturing solution were unique to the isolation of miRNA in solution. Moreover, it was observed that heparin cannot be used in the instant method. Based upon the analysis described herein, the yield of miRNA from serum using the instant isolation method and kit is higher compared to conventional TRIZOL regents (2.88±0.48 µg/ml vs. 2.38±0.41 µg/ml).

The instant method for isolating solution miRNA, includes the steps of (a) incubating a biological sample containing miRNA in a denaturing solution containing 20-25 mM sodium citrate and glycogen; and (b) extracting the miRNA. In addition, conventional reagents such as guanidinium thiocyanate and 2-mercaptoethanol can be used as protein denaturants and Sarkosyl can be used as a surfactant. Likewise, conventional reagents such as chloroform and isopropyl alcohol can be used to extract the miRNA. More specifically, the reagents of the instant miRNA isolation method and kit are listed in Table 1.

TABLE 1

| Solution | Amount in Kit | Components |
|---|---|---|
| Solution A (Denaturing Solution) | 75 mL | 4M Guanidinium Thiocyanate 22 mM Sodium Citrate, pH 7.0 0.5% (wt/vol) N-laurosylsarcosine (Sarkosyl) 1M 2-mercaptoethanol 2 µg/ml Glycogen |
| Solution B (Phase separation solution) | 20 mL | Chloroform |
| Solution C (Precipitation solution) | 50 mL | Isopropyl Alcohol |
| Solution D (Washing solution) | 100 mL | 75% Alcohol |
| Solution E (Dissolving solution) | 50 mL | DEPC-treated water |

In general, the reagents of the instant quantitation kit include components for quantitative real-time polymerase chain reaction and mature miRNA for generating a standard curve. The instant method for quantitating solution miRNA, includes the steps of (a) reverse transcribing the miRNA; (b) subjecting the reverse transcribed product of (a) to real time PCR; and (c) comparing the amount of real time PCR product of (b) with a reference amount of mature miRNA to quantitate the miRNA. More specifically, the reagents of the instant miRNA quantitation method and kit are listed in Table 2.

TABLE 2

| Solution F (miRNA RT Master Mix) | 3 mL | 2X RT Buffer 2X miRNA RT Primers 0.6 U/µL RNase Inhibitor 2 U/µL Reverse Transcriptase |
|---|---|---|
| Solution G (miRNA PCR Master Mix) | 3 mL | 2XPCR buffer (containing SYBR Green I for Real time PCR) 0.1 U/µL Taq DNA Polymerase 0.8 mM dNTP Mix 500 nM miRNA PCR primers |
| Solution H (miRNA standard solution) | 100 µL | 1.00E−7 mol/L mature miRNAs |

In addition to the above-referenced reagents, the instant kits can further include additional buffers, diluents, stabilizers and other reagents, in the same or separate containers, as well as instructions for carrying out the instant methods.

Establishing a method to determine the absolute amount of a miRNA in blood is the prerequisite for blood miRNA study. Unlike tissue, which has many good markers such as U6 for normalization and calculating the amount of tissue miRNAs, blood lacks this kind of internal control for miRNA normalization. Although there are some reports using RNAs such as 18S, 5S, snoRNA (small nucleolar RNA) U38B, snoRNA U43, snRNA (small nuclear RNA) U6 and other miRNAs as the internal controls for normalization, the levels of these control makers can often change, especially under pathological conditions. It has now been found that the serum (plasma or blood) volume as normalization (pmol/l) is of use in determining the levels of miRNAs in blood. The amount of molecules per ml or per liter of biological fluid (e.g., serum, plasma or blood) is also the standard method of evaluating the blood levels of other molecules in the clinic.

Using the instant methods and kits, the concentration of miR-1 in normal serum was determined. The results showed excellent linearity between the log of target input and CT value (i.e., the cycle number at which the fluorescence signal associated with a particular amplicon accumulation crosses the threshold), indicating that the instant methods and kits are capable of detecting a dynamic range in the qRT-PCR. Indeed, using this quantitative method, the absolute amount of a miRNA in serum could be determined at nmol/L to pmol/l levels. Moreover, using the instant methods and kits, it was found that miR-1 is a useful biomarker in acute myocardial infarction.

Heart damage occurs in ischemic heart disease (acute myocardial infarction and angina), ischemia-reperfusion injury induced by intravenous thrombolytic therapy, percutaneous transluminal coronary angioplasty (PTCA) and coronary artery bypass grafting (CABG), heart transplantation, heart failure, myocarditis, and cardiomyopathy. Identifying heart-specific damage markers in blood is therefore critical to diagnosis and prognosis of heart diseases. Accordingly, the instant invention also provides methods for diagnosing the occurrence of an acute myocardial infarction and determining the prognosis of a patient after an acute myocardial infarction by detecting the presence, or more particularly the quantity, of miR-1 in a biological fluid.

The results herein indicate that cardiac miR-1 is able to be released and the released amount is associated with the extent of cardiac cell damage. Moreover, the released miR-1 is stable, a feature that is important for a circulating disease biomarker. Indeed, the results herein indicate that incubation of serum at room temperature for up to 4 hours, or subjecting serum to up to several freeze-thaw cycles, had no significant effect on endogenous miR-1 levels, although the serum contained high levels of RNase activity. Thus, serum miR-1 is a stable biomarker. Not wishing to be bound by theory, it is contemplated that endogenous miR-1 binds other materials, either in blood or in released cells, e.g., exosomes, because it was observed that exogenous mature miR-1 was quickly degraded both in vitro and in vivo.

Furthermore, in the clinical analysis, it was found that serum miR-1 in patients with AMI was quickly increased within hours of presentation. In patients within 24 hour of AMI, there was an increase in miR-1 serum levels of over 20-fold. In addition, there was a positive relationship between serum miR-1 and CK-MB. The result indicated that serum miR-1 is related to myocardial infarct size in humans. In addition, on the basis of the animal study, the time course change in miR-1 was similar to that of CK-MB in AMI, but is different from that of TnT (troponin T). In patients at 3 and 7 days after AMI, the serum level returned to the basal level. Thus, miR-1 is of use as an early biomarker for AMI.

For diagnostic or prognostic purposes, biological samples, such as serum or plasma, can be obtained from any mammalian source including human, mouse, dog, cat, or horse subjects. Any number of appropriate primers can be designed from the polynucleotide sequences encoding miR-1. However, in particular embodiments, the primer used in accordance with the instant method and kit is that of SEQ ID NO:1. The diagnostic and prognostic methods of the instant invention include detecting the presence or more particularly the relative or absolute amount of miR-1 in a biological fluid and comparing the detected amount with a reference sample, wherein elevated amounts of miR-1 in the biological fluid as compared to the reference sample indicate that the subject had an acute myocardial infarction. An elevated or increased amount of miR-1 in a biological fluid is intended to mean at least a 5-, 10-, 50-, 75-, 100-, 150- or 200-fold increase in miR-1 levels as compared with a normal reference sample (e.g., serum levels in a healthy subject). For example, as the results herein indicate, normal serum has very low miR-1 levels (e.g., 8.83±1.28 ng/L or 1.63±2.36×10$^{-14}$ mol/L in rats), whereas within an hour after AMI, miR-1 levels significantly increase (e.g., 194±112 ng/L or 3.58±2.06×10$^{-13}$ mol/L in rats). Indeed, even after 24 hours of AMI, amounts of miR-1 are at least 10-fold higher than healthy controls (see, e.g., FIG. 2A). Therefore, the instant method can be carried out within one, two, three, four, five or six hours of AMI, or up to 24 hours after AMI.

Moreover, given that serum miR-1 levels correlate with myocardial infarct size (see FIG. 1), the extent of cardiac damage can be assessed to identify subjects at a higher risk of adverse outcome. It is contemplated that the instant prognostic method can use the amount of miR-1 alone as a factor in identifying subjects at risk of an adverse outcome. Alternatively, the instant method can be used in combination with other risk stratifying factors including, but not limited to, age, hemodynamic parameters (such as heart failure, cardiac arrest on admission, systolic blood pressure), ST-segment deviation, diabetes, serum creatinine, peripheral vascular disease and elevation of other cardiac markers such as CK-MB.

In addition to AMI, the instant method steps and kit also find application in detecting heart damage in other diseases such as unstable angina, ischemia-reperfusion injury induced by intravenous thrombolytic therapy, PTCA and CABG, heart transplantation, heart failure, myocarditis, and cardiomyopathy.

The invention is described in greater detail by the following non-limiting examples.

Example 1

Materials and Methods

AMI, IP (Ischaemic Preconditioning) and I/R (Ischaemia/Reperfusion) Injury in Animal Models. AMI, IP and I/R injury in rats were induced by LAD (left anterior descending coronary artery) ligation, as described in the art. In brief, 10-week-old male Sprague-Dawley rats (weighing 250-300 grams) were anaesthetized with ketamine (80 mg/kg of body weight, i.p. (intraperitoneally)) and xylazine (5 mg/kg of body weight, i.p.). Under sterile conditions, an anterior transmural AMI was created by occlusion of the LAD with a silk suture. Sham-operated rats served as controls. Sham operation involved an identical procedure, except the suture was passed around the vessel without LAD occlusion. IP was achieved via four cycles of 5 minutes of LAD occlusion/5 minutes of reperfusion cycles. I/R injury was induced in rat hearts via 1 hour of LAD occlusion/3 hours of reperfusion. The animals were divided into three study groups. Group 1 was for the time course study of serum miR-1. In this group, the blood samples were obtained via tail vein from rats before (0 hour) and at 1 hour, 3 hours, 6 hours, 12 hours, 24 hours, 3 days, 7 days, 14 days, 21 days and 28 days after AMI. Eight rats were used in the time course study. In addition, eight sham-operated rats were used as the controls. Group 2 had 12 rats, which were used to study the relationship between serum miR-1 and myocardial infarct size induced by I/R injury. Group 3 was used to study the effect of IP on serum miR-1 and myocardial infarct size induced by I/R injury, in which six sham operated rats, six I/R rats and six IP I/R rats finished the experiment.

Measurement of Infarct Size. Myocardial infarct size was determined by pathological staining, which is the gold standard for AMI. At the end of experiments, rats were anaesthetized and 6 ml of 10% Evans Blue dye was injected into the vena cava to define the area that was not supplied by LAD. The myocardial IAR (ischaemic area at risk) was identified as the region lacking blue staining. The ventricles of the hearts were sliced transversely into 2-mm-thick slices. The slices were incubated in 1% TTC (triphenyltetrazolium chloride) at 37° C. for 10 minutes to identify the non-infarcted and infarcted areas. TTC staining was displayed as a red color. The infarcted area was defined as the TTC unstained area (white color). Infarct size was expressed as a percentage of the IAR.

Blood Sample Collection, Serum miRNA Isolation and Establishing the Quantitative Method for miR-1 Assay. Before and at different times after AMI, IP, I/R injury or sham surgery, the blood samples were collected from a tail vein. The samples were placed for 1 hour at room temperature (26° C.) and were then centrifuged at 1600 g for 20 minutes at 4° C. Serum samples were carefully transferred into plain propylene tubes and stored at 70° C. until miRNA isolation. miRNAs were isolated in 200 μl of serum using miRNAs Isolation Kit solution. In brief, miRNAs in serum were first denatured by denaturing solution (Solution A) and were separated by phase-separation solution (Solution B). Then, the samples were processed using precipitation solution (Solution C), washing solution (Solution D) and dissolving solution (Solution E). miR-1 was measured by qRT-PCR with a ROCHE LIGHTCYCLER 480 Detection System using the primer 5'-gtc gta tcc agt gcg tgt cgt gga gtc ggc aat tgc act gga tac gac tac ata c-3' (SEQ ID NO:1).

Specifically, miRNA were isolated by:
1. Adding 0.75 ml of Solution A per 0.25 ml sample, mixing well and incubating 10 minutes at 4° C.
2. Adding 0.2 ml Solution B, vortexing 20 seconds, and incubating 2 minutes at 4° C.
3. Centrifuging the sample at 12,000×g for 15 minutes at 4° C.
4. Transferring 0.35 ml of the upper aqueous phase to a new 1.5 ml RNase-free tube.
5. Adding 0.4 ml of Solution C to the upper aqueous phase and mixing well.
6. Incubating the sample at −20° C. for two or more hours.
7. Centrifuging the sample at 12,000×g centrifuge for 30 minutes at 4° C.
8. Removing the supernatant, washing the RNA pellet once with 1 ml of cold Solution D, and centrifuging the sample at 12,000×g for 5 minutes at 4° C.
9. Air-drying the RNA pellet for 10 minutes at room temperature.
10. Adding 0.1 ml of Solution E and incubating the sample for 10 minutes at 4° C. (RNA solution).
11. Adding 10 µl of Solution F to 10 µl of the RNA solution, mixing well, and carryout out the reverse transcriptase reaction by incubating the sample at 16° C. for 40 minutes, 42° C. for 40 minutes; and 85° C. for 5 minutes).
12. Adding 100 µl of Solution E to the reverse transcriptase reaction sample and mixing well.
13. Adding 10 µl of Solution G per 10 µl of the reverse transcriptase reaction sample, mixing well, centrifuging shortly, and carrying out Real-time PCR by incubating the sample at 95° C. for 10 minutes, repeating 50 cycles at 95° C. for 15 seconds, and incubating at 60° C. for 1 minute).
14. Diluting Solution H to different concentrations and carrying out the qRT-PCR as in steps 11 to 14.

The same isolation and assay were performed using a series of concentrations of reference miR-1 (synthesized by IDT, Coralville, Iowa) to make a standard curve. The absolute amount of miR-1 was calculated by software based on serum sample qRT-PCR numbers and the standard curve, and were expressed as pmol/l.

MiRNA Expression Signature Assay. To verify the specific expression of miR-1 in the heart, miRNAs were isolated from rat heart, aorta and lung using MIRVANA miRNA isolation kit (AMBION) and an miRNA expression signature was performed by miRNA microarray analysis using a chip containing 341 mature miRNAs (Chip ID miRRat 12.0 version; LC Sciences), as described in the literature. In addition, the miR-NAs in rat heart, aorta, lung, liver, brain, small intestine and kidney were also isolated for miR-1 assay.

Cell Culture. Primary cultures of neonatal rat cardiac ventricular myocytes were performed as described in the literature. In brief, hearts from 1-2 day-old Sprague-Dawley rats were removed after hypothermia anaesthesia immersion in ice water and placed in ice-cold 1×PBS solution. After repeated rinsing, the atria were removed, and the ventricles were minced with scissors. The minced tissue and ventricular cells were dispersed by digestion with collagenase type IV (0.45 mg/ml), 0.1% trypsin, and 15 µg/ml DNase I. Cardiomyocytes ($0.33 \times 10^6$ cells/ml) were cultured in cardiac myocyte culture medium (Dulbecco's Modified Eagle's Medium supplemented with 10% (v/v) fetal bovine serum, 4 µg/ml transferrin, 0.7 ng/ml sodium selenite, 2 g/l BSA (fraction V), 3 mmol/l pyruvic acid, 15 mmol/l HEPES, 100 µmol/l ascorbic acid, 100 µg/ml ampicillin, 5 µg/ml linoleic acid, 1% penicillin, 1% streptomycin and 100 µmol/l 5-bromo-2'-deoxyuridine), and seeded into six-well plates.

Necrosis Model of Cultured Cardiac Myocytes and miR-Release Assay. The necrosis model of cultured cardiac myocytes was induced by TRITON X-100. Briefly, rat cardiac myocytes in six-well plates cultured with 10% (v/v) fetal bovine serum were washed three times with 0.01 M phosphate-buffered saline (PBS) to remove medium and serum. Then, the cells were treated for 20 minutes at room temperature with different concentrations of TRITON X-100 (0.25, 1 and 2%) diluted in 0.1% sodium citrate. As a negative control, the cells were incubated with PBS alone (vehicle). After treatment, the culture supernatant from each well was collected for the miR-1 assay. In addition, in the 2% TRITON X-100-treated group, the supernatants were kept at 37° C. for 6, 12 and 24 hours for the stability assay of miR-1.

Clinical Study. AMI was defined as (i) chest pain characteristic of myocardial ischaemia for 30 minutes or more, (ii) ST segment elevation within 6 hours of chest pain at least 0.1 mV in at least two leads of the ECG, and (iii) confirmation of the diagnosis of AMI by elevated by CK-MB (creatine kinase-MB) isoenzyme in serum, which was at least twice the normal range. Blood samples from patients without the confirmation of AMI were not used in the present study. In total, 31 patients with AMI were used (18 men and 13 women; mean age, 57±0.1 years (range, 45-71 years)). Of these, 20 had coronary angiography data showing at least one-vessel disease. Among the patients studied, 11 had hypertension and were being treated with antihypertensive medication, an AngII (angiotensin II) receptor inhibitor and/or β-blocker; and eight patients had hyperlipidaemia and were being treated with simvastatin. No patients with diabetes were included in the present study. Blood samples were obtained within 24 hour of AMI. The time interval between the onset of typical chest pain and blood samples was 8.5±3.82 hours. Blood samples obtained from 20 age- and gender-matched healthy volunteers were used as controls. All the blood samples were placed for 1 hour at room temperature and were centrifuged at 1600 g for 20 minutes at 4° C. Serum miR-1 levels were determined as described above. CK-MB was determined using an immunoinhibition assay method (Roche Diagnostics; normal range, 0-25 units/l).

Statistics. All results are presented as means±S.E.M. For relative gene expression, the mean value of the vehicle control group was defined as 100% or 1. Two-tailed unpaired Student's t tests and ANOVA were used for statistical evaluation of the data. Linear regression analysis was used to determine the relationship between myocardial infarct size and serum miR-1, and the relationship between serum CK-MB and serum miR-1. The SIGMASTAT statistical analysis program was used for data analysis. A P value <0.05 was considered significant.

Example 2

Results miR-1 is a Heart-Selective miRNA and is the Most Abundant miRNA in Normal Rat Hearts. Microarray analysis of miRNAs in the heart revealed that miR-1 was the most abundant miRNA in normal rat hearts; however, the expression of miR-1 in aorta and lung samples was almost undetectable. The average microarray signal of miR-1 in heart was 51191.30, whereas in lung and aorta the signals were only 62.12 and 31.23, respectively. To further verify the heart selectivity of miR-1 expression, miR-1 levels in rat liver, brain, small intestine and kidney were determined by qRT-PCR. No significant miR-1 expression was found in these tissues.

miR-1 is Released by Necrotic Cardiac Myocytes in vitro. Given that miR-1 is the most abundant miRNA in the normal heart, it was posited that the trace amount of miR-1 released into the circulating blood under physiological conditions may be responsible for the low basal serum level of miR-1. Therefore, levels of miR-1 were determined for necrotic myocytes. The results of this analysis indicated that necrosis of cardiac myocytes was induced by TRITON X-100 and miR-1 was released into the culture medium at 20 minutes after treatment with TRITON X-100. The amount of miR-1 release was related to the number of necrotic cardiac myocytes, as increased miR-1 levels were found with the increasing concentrations of TRITON X-100 (0.25%, 1%, and 2%). Moreover, the released miR-1 was stable in culture solution for at least 24 hours.

Establishing a Quantitative Method to Assay miR-1 in Blood. The linear range was determined by analysis of synthesized standard miR-1, normal rat serum miR-1 and serum miR-1 from rats following AMI. CT values (i.e., the cycle number at which the fluorescence signal associated with a particular amplicon accumulation crosses the threshold) of the standard curve were plotted against the logarithmic concentration of the serial dilutions of the isolated miR-1. For example, a representative standard curve of these assays had a correlation coefficient of $R^2$=0.99 and efficient amplification with a slope of −3.4573 for all of the experiments. The assay was linear over a range of 0.01 to 10 μmol/1 miR-1.

Serum miR-1 is a Novel Biomarker for AMI. AMI was induced by LAD ligation as demonstrated using a pathological staining method. In serum from the sham group (normal), the miR-1 level was low and was barely detectable using the highly sensitive qRT-PCR method (0.016±0.008 pmol/l). Interestingly, serum miR-1 levels were significantly increased to 3.67 pmol/l in rats at 6 hours after AMI. To determine the time course of changes in miR-1 after AMI, serum miR-1 levels were determined before (0 hours), and at 1 hour, 3 hours, 6 hours, 12 hours, 24 hours, 3 days, 7 days, 14 days, 21 days and 28 days after AMI in eight rats. Compared with normal controls (sham and 0 hour groups), serum miR-1 levels were rapidly increased, peaking at 6 hours after AMI, at which an increase in miR-1 levels over 200-fold was demonstrated. Specifically, it was found that in normal rat serum, the miR-1 level was very low (8.83±1.28 ng/L or 1.63±2.36×$10^{-14}$ mol/L). However, after AMI, the serum levels of miR-1 were quickly increased. At 1 hour after AMI, the miR-1 level was increase to 194±112 ng/L (3.58±2.06×$10^{-12}$ mol/L). At 3 hours after AMI, the miR-1 level was 821±128 ng/L (1.52±0.24×$10^{-12}$ mol/L). Six hour after AMI, the miR-1 level reached the peak with 2010±162 ng/L (3.72±0.3×$10^{-12}$ mol/L). The miR-1 levels in serum at 24 hours after AMI were still at higher concentrations 312±143 ng/L (5.76±2.64×$10^{-13}$ mol/L). Three days after AMI, The miR-1 levels returned to the normal levels.

Serum miR-1 Levels are Associated with Myocardial Infarct Sizes. To determine the relationship between serum miR-1 levels and myocardial infarct sizes, the infarct sizes induced by I/R injury and serum miR-1 levels were determined in 12 rats. This analysis demonstrated a strong positive correlation between the two variables (r=0.88; P<0.05; slope 0.184; FIG. 1). IP Reduces Myocardial Infarct Size and Serum miR-1 Levels. To further determine the relationship between serum miR-1 levels and myocardial infarct size, IP was performed on rat hearts prior to I/R injury. This analysis indicated that AMI was induced by I/R injury. Accordingly, serum miR-1 levels were significantly increased in rats following I/R injury. As expected, myocardial infarct size was significantly reduced by IP (from approximately 50 to 24). Interestingly, serum miR-1 levels induced by I/R injury were also inhibited by IP (from approximately 10 μmol/L to 4 pmol/L).

Figure 2A:
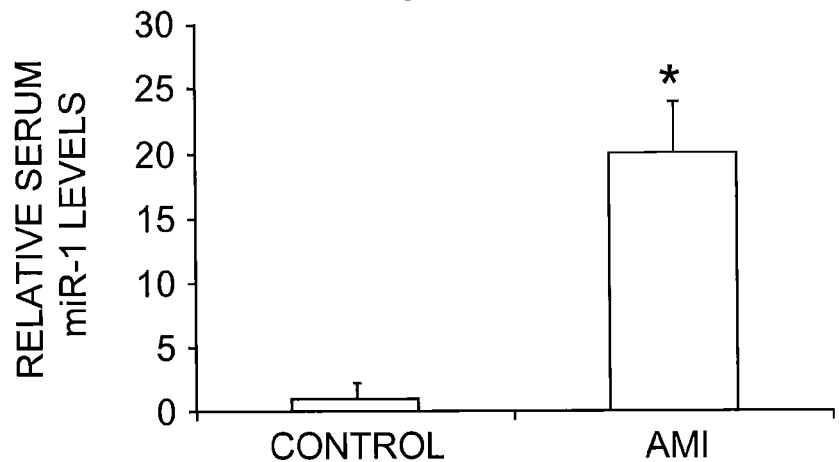
(FIG. 2A) Serum miR-1 levels were determined from patients (n=31) within 24 hours of AMI. The serum from age-matched healthy controls (n=20) was used as the control group. Values are means±S.E.M.; *P<0.05 compared with the control group.
Figure 2B:
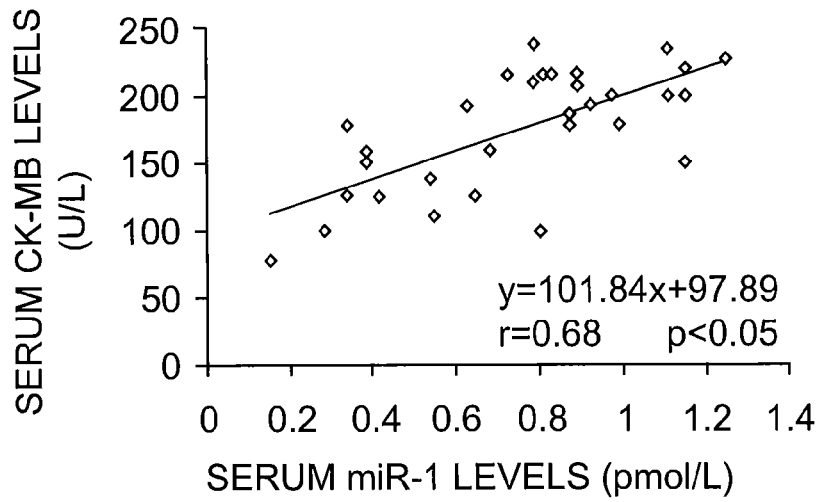
(FIG. 2B) The relationship between serum miR-1 levels and CK-MB levels in patients (n=31). A positive correlation was demonstrated between the two variables (r=0.68; P<0.05).

Serum miR-1 Levels are Significantly Increased in Patients with AMI. Serum miR-1 levels from 31 patients within 24 hours of AMI were significantly increased compared with healthy controls (FIG. 2A). Among them, a nearly 100-fold increase in serum miR-1 was found in patients at 6 hours after AMI. The release of miR-1 into the circulation was very rapid, as the increase in serum miR-1 was found in patients within hours of presentation. No increase in serum miR-1 levels was found in patients at 3 and 7 days after AMI. To investigate the potential relationship between serum miR-1 levels and myocardial infarct sizes in humans, CK-MB levels in these patients were also determined. This analysis demonstrated a positive correlation between serum miR-1 and CK-MB levels (r=0.68; P<0.05; slope=101.84; FIG. 2B).

The results presented herein are of significance not only for cardiovascular diseases, but also for other diseases. Based on high sensitive real-time PCR and standard curve of mature miRNAs, a robust absolute quantitative assay kit for measuring miRNAs in a solution is now available.

What is claimed is:

1. A kit for isolating and analyzing miRNA from a biological fluid comprising
    (a) a denaturing solution containing 20-25 mM sodium citrate and glycogen;
    (b) extraction reagents;
    (c) reverse transcriptase (RT) and an RT primer of SEQ ID NO:1;
    (d) reagents for real time PCR; and
    (e) mature miRNA.

2. The kit of claim 1, wherein the mature miRNA is mature miR-1.

3. A method for diagnosing or prognosing an acute myocardial infarction comprising
    (a) providing a blood or plasma sample from a subject;
    (b) quantitating the amount of miR-1 in the subject's sample using a primer of SEQ ID NO:1; and
    c) comparing the amount of miR-1 in the subject's sample with the amount of miR-1 in a reference sample, wherein an increase in the amount of miR-1 in the subject's sample compared with the reference sample is indicative of an acute myocardial infarction diagnosis or prognosis.

4. The method of claim 3, wherein the amount of miR-1 is indicative of the amount of cardiac damage.

5. The method of claim 3, wherein the amount of miR-1 is determined within 24 hours of the myocardial infarction.

* * * * *